United States Patent
Davis et al.

(10) Patent No.: US 6,938,319 B2
(45) Date of Patent: Sep. 6, 2005

(54) METHOD OF ASSEMBLING AN ACTUATING MECHANISM FOR A FLUID PRESSURIZING DEVICE

(75) Inventors: Richard M. Davis, Guntersville, AL (US); Rowland W. Kanner, Guntersville, AL (US)

(73) Assignee: Atrion Medical Products, Inc., Arab, AL (US)

( * ) Notice: Subject to any disclaimer, the term of this patent is extended or adjusted under 35 U.S.C. 154(b) by 0 days.

(21) Appl. No.: 10/897,932

(22) Filed: Jul. 23, 2004

(65) Prior Publication Data

US 2004/0255448 A1 Dec. 23, 2004

Related U.S. Application Data

(62) Division of application No. 10/045,392, filed on Nov. 9, 2001, now Pat. No. 6,796,959.
(60) Provisional application No. 60/277,115, filed on Mar. 19, 2001.

(51) Int. Cl.$^7$ .................................................. B23P 11/00
(52) U.S. Cl. ........................................................ 29/434
(58) Field of Search ........................ 29/434, 436, 450, 29/525.01

(56) References Cited

U.S. PATENT DOCUMENTS

| | | |
|---|---|---|
| 4,370,982 A | 2/1983 | Reilly |
| 4,723,938 A | 2/1988 | Goodin et al. |
| 4,838,864 A | 6/1989 | Peterson |
| 4,940,459 A | 7/1990 | Noce |
| 5,137,514 A | 8/1992 | Ryan |
| 5,168,757 A | 12/1992 | Rabenau et al. |
| D342,263 S | 12/1993 | Harrell, Jr. |
| D343,397 S | 1/1994 | Wang |
| D348,677 S | 7/1994 | Phillips et al. |
| D351,896 S | 10/1994 | Sundheim et al. |
| D358,397 S | 5/1995 | Phillips et al. |
| 5,507,727 A * | 4/1996 | Crainich .................. 604/97.02 |
| D375,315 S | 11/1996 | Paul-Johansson |
| 5,713,242 A | 2/1998 | Kanner et al. |
| D392,650 S | 3/1998 | Zarnowitz |
| 6,106,496 A * | 8/2000 | Arnissolle ................ 604/97.01 |
| 6,110,151 A | 8/2000 | Spool et al. |
| D454,358 S | 3/2002 | Davis et al. |

FOREIGN PATENT DOCUMENTS

WO    WO9217221    10/1992

* cited by examiner

Primary Examiner—David P. Bryant
(74) Attorney, Agent, or Firm—Trexler, Bushnell, Giangiorgi, Blackstone & Marr, Ltd.

(57) ABSTRACT

An actuating mechanism for rapidly and selectively moving a threaded screw and nut member combination into or out of threaded engagement, particularly for use to pressurize angioplasty balloon catheters, or the like. The mechanism includes a housing and a threaded screw structure slidably displaceable through the housing. A nut member having partial threads is selectively engageable and disengageable with the threaded screw structure. The mechanism includes a carrier member and is designed to be assembled from the rear. The carrier member is preferably configured to be retainably engaged with the housing via a bayonet arrangement, such as a quarter-turn bayonet arrangement, and is configured to provide an audible indication when it is, in fact, properly and fully installed. Preferably, the housing is configured to receive a pressure gauge directly into a threaded bore on the housing. An improved method of assembling an actuating mechanism is also provided.

4 Claims, 9 Drawing Sheets

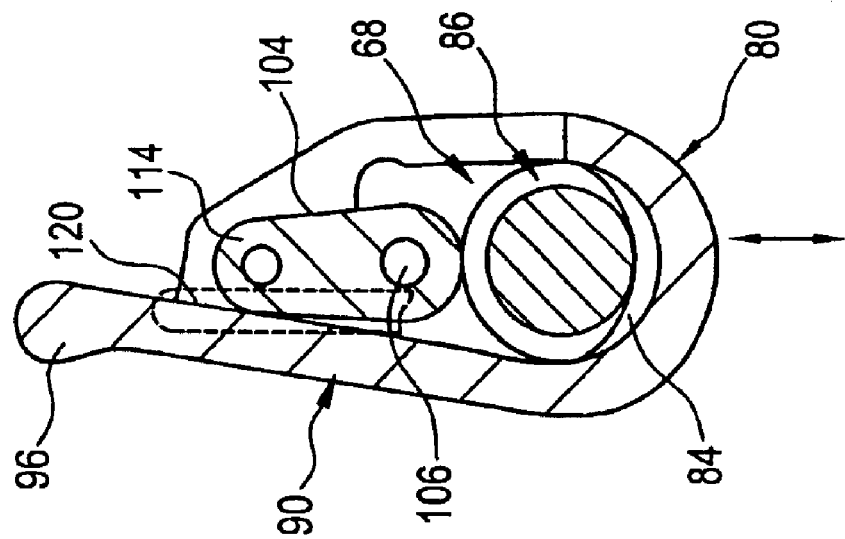
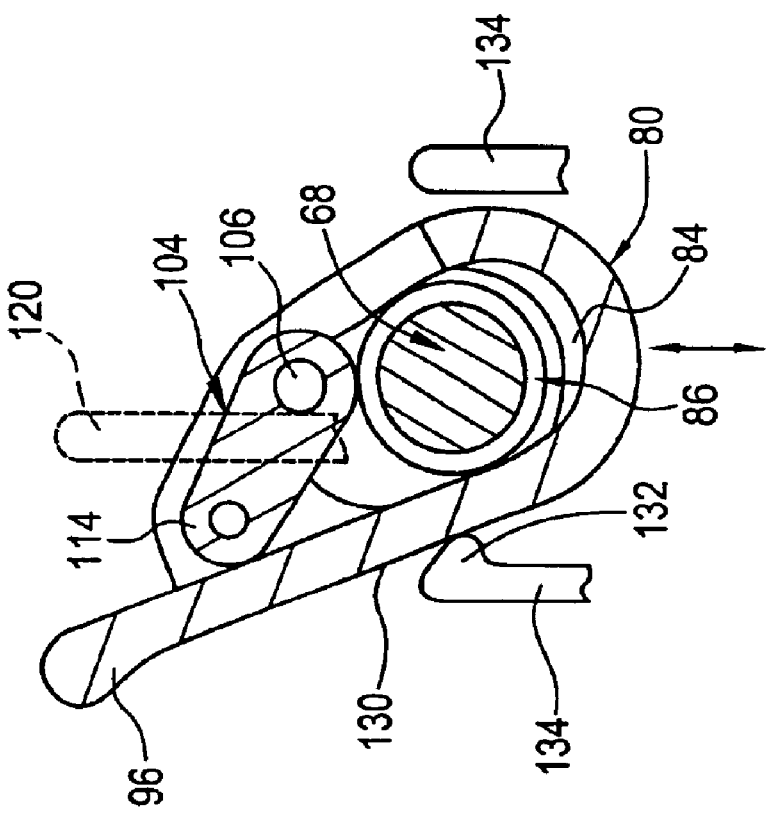

METHOD OF ASSEMBLING AN ACTUATING MECHANISM FOR A FLUID PRESSURIZING DEVICE

RELATED APPLICATION

This is a divisional of application Ser. No. 10/045,392, filed on Nov. 9, 2001 now U.S. Pat. No. 6,796,959.

This application claims also the benefit of U.S. Provisional Application Ser. No. 60/277,115, filed Mar. 19, 2001.

BACKGROUND

This invention relates to fluid pressurizing devices for balloon catheters or the like, and more particularly relates to an improved device for actuating a screw plunger and monitoring the resulting fluid pressurization.

Fluid pressurization devices adapted for selectively applying and relieving a measured pressure on a closed volume of fluid have been developed for use in inflation and deflation of a balloon catheter used in angioplasty balloon procedures interiorly of blood vessels, or other types of balloon catheterization procedures. For example, U.S. Pat. No. 4,838,864 discloses a syringe device which inflates and deflates a catheterized balloon. The device uses a manually-operated screw plunger to achieve or maintain specific balloon pressure, and the pressure is monitored using an associated pressure gauge. Improved syringing and pressurization control is also described in U.S. Pat. Nos. 5,168,757 and 5,713,242, both of which are incorporated herein in their entirety by reference. The '757 and '242 patents disclose quick release mechanisms which enable rapid advancement of a threaded screw plunger and alternatively allow threaded engagement with the screw plunger to achieve precise control during final pressurization of a balloon catheter.

A cross-sectional view of the device which is disclosed in U.S. Pat. No. 5,713,242 is shown generally in FIG. 1 (FIG. 1 corresponds to FIG. 2 of the '242 patent). As shown, the device 10 provides that a piston 12 is engaged with a plunger 14 inside a fluid displacement chamber 16 provided in a housing 18. The design of the device 10 (see specifically walls 20 and 22 of the housing 18) is such that the piston 12 must be front-loaded into the fluid displacement chamber 16. More specifically, the piston 12 is slid into the front 24 of the fluid displacement chamber 16, from left-to-right in FIG. 1, and then a fitting 26 and a clamping cover 28 is engaged and sealed with the end of the housing 18 to close off the end 24 of the fluid displacement chamber 16. It is important to provide that the chamber 16 is sealed because the chamber 16 becomes pressurized when the device 10 is in use. The fitting 26 carries a gauge 30 which is configured to monitor the pressure of the chamber 16 while the device 10 is used. Because the clamping cover 28 and fitting 26 are parts which are distinct from the housing 18, the parts must be manually handled, which complicates the assembly process and consumes labor. Additionally, these extra parts, being located at the distal end (i.e. the end where the clamping cover 28 and fitting 26 are located) of the device 10, may obstruct the view of a physician who is attempting to purge the device by getting all the air bubbles out of the chamber 16.

The present invention is an improvement on this prior art design as it involves a construction which permits the unit to be assembled entirely from the rear. Thus, the main housing, including the forward portion that receives and supports the pressure gauge can be fabricated as a single, integral component. Additionally, the design provides that many of the parts are universal such that they are compatible with devices of different sizes.

OBJECTS AND SUMMARY

An object of an embodiment of the present invention is to provide an improved device for actuating a screw plunger and monitoring the resulting fluid pressurization.

Another object of an embodiment of the present invention is to provide an improved structure and process for assembling a fluid displacement device.

Still another object of an embodiment of the present invention is to provide a fluid displacement device which is relatively easy to assemble.

Another object of an embodiment of the present invention is to provide a fluid displacement device which includes a housing which directly receives a pressure gauge, without requiring an extra fitting.

Still yet another object of an embodiment of the present invention is to provide a fluid displacement device which is configured to withstand intense chamber pressure during use.

Another object of an embodiment of the present invention is to provide a fluid displacement device which includes a carrier member that is configured to provide an audible indication when it is properly and fully installed on the device.

Still yet another object of an embodiment of the present invention is to provide a fluid displacement device which provides high visibility at a distal end, thereby allowing a user to eliminate any air bubbles while priming the device for use.

Still yet another object of an embodiment of the present invention is to provide a fluid displacement device which is designed such that many of the parts are universal such that they are compatible with devices of different sizes.

Briefly, and in accordance with at least one of the foregoing objects, an embodiment of the present invention provides an actuating mechanism for rapidly and selectively moving a threaded screw and nut member combination into or out of threaded engagement, particularly for use of the screw as a control fluid plunger to pressurize balloon catheters, or the like. The mechanism includes a housing and a threaded screw structure slidably displaceable through the housing. A nut member having partial threads is selectively engageable and disengageable with the threaded screw structure. The nut member is configured to enable selective movement of the nut member relative to the screw structure to provide selective threaded engageability of the partial threads with the screw structure. At least a portion of the nut member is disposed in a carrier member, and the carrier member is disposed generally in the housing.

The mechanism includes a plurality of link members, at least one of which is engaged with the nut member. Link structure is configured to couple the carrier member to the link members, thereby providing that the nut member and link members are pivotable relative to the carrier member. Preferably, the carrier member is disposed proximate one end of the housing, and an opposite end of the housing is configured to receive a pressure gauge directly into a threaded bore. The carrier member is preferably configured to be retainably engaged with the housing via a bayonet arrangement, such as a quarter-turn bayonet arrangement. Additionally, preferably the carrier member is configured to provide an audible indication when it is, in fact, properly and fully installed. The audible indication may be provided by a latching finger on the carrier member which engages corresponding structure on the housing. Preferably, engagement of the latching finger on the carrier member with the retaining structure on the housing provides that the carrier member does not readily rotate (i.e. counter rotation) relative to the housing.

Preferably, the nut member is bifurcated to provide a pair of opposingly spaced mounting portions extending from the partially threaded portion of the nut member. The mounting portions are effectively coupled to the housing by a pair of adjacently arranged link members which are separately coupled to the respective mounting portions and are disposed therebetween while being operable in tandem to guide translating motion of the nut member. The nut member preferably moves in a plane in a diminishing curved path in traveling between an engaged position and a disengaged position.

Preferably, the carrier member is received in a bore in the housing and a radius of the bore is larger than a distance from a center line of the threaded screw structure to the link structure which engages the carrier member. The carrier member provides that the device is assembled by rear loading the piston into the fluid displacement chamber provided in the housing.

Another aspect of the present invention provides a method of assembling an actuating mechanism. The assembly method includes engaging a hose with a housing, engaging a gauge with the housing, placing a sealing member on a piston, sliding the piston into the housing from the back end of the housing, sliding a carrier member into the housing through a back end of the housing, rotating the carrier member thereby providing that the carrier member generally locks in place with respect to the housing, installing link members in a nut member, placing the nut member generally into the carrier member, engaging a pivot pin with the carrier member and the link members, sliding a plunger into the back end of the housing through the nut member and carrier member, and engaging the plunger with the piston.

As mentioned above, this permits the housing to be fabricated, as by molding, as a single component. This not only reduces the cost of the components and molds, but facilitates assembly, thereby reducing labor costs, all of which is achieved with the structure illustrated and described hereinafter.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIGS. 6 and 7 are enlarged sectional views of the actuating mechanism shown in FIGS. 2–5, showing two reversible operating positions of the actuating mechanism;

DESCRIPTION

Figure 1:
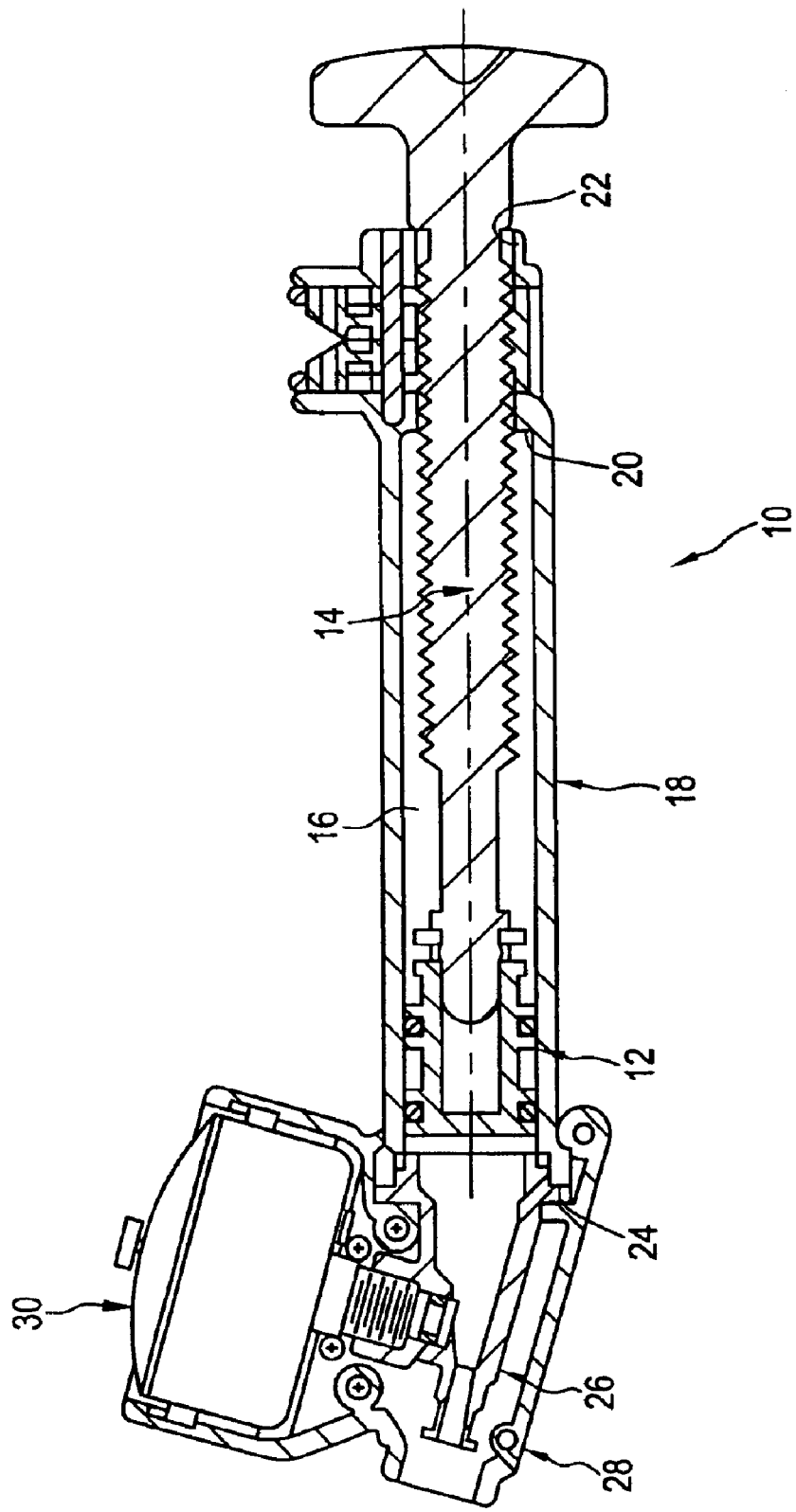
FIG. 1 is a cross-sectional view of a prior art actuating mechanism.
Figure 2:
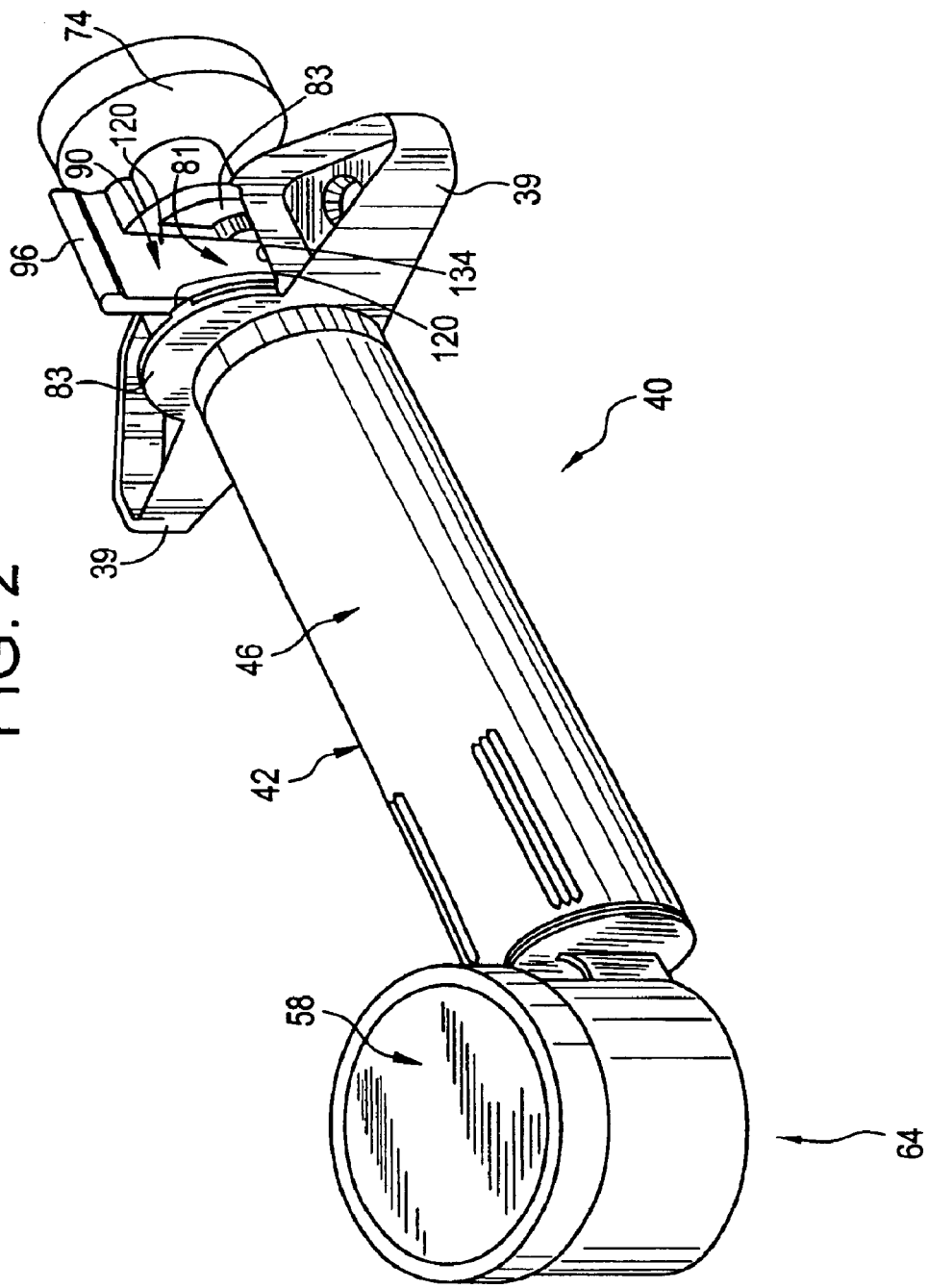
FIG. 2 is a perspective view of an actuating mechanism which is in accordance with an embodiment of the present invention.
Figure 3:
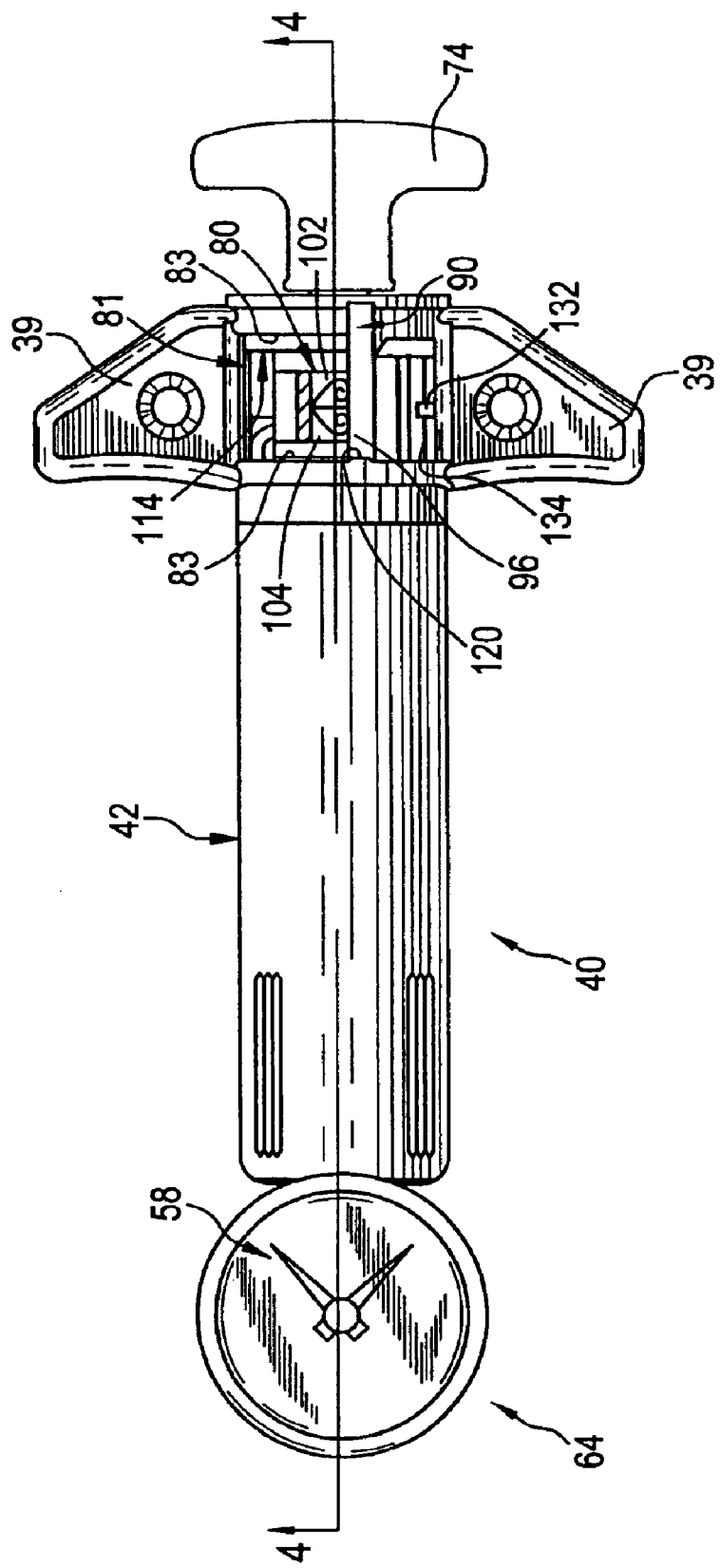
FIG. 3 is a top plan view of the actuating mechanism illustrated in FIG. 2.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

Shown in FIGS. 2–5 is an actuating mechanism, specifically a fluid displacement device 40 which is in accordance with an embodiment of the present invention. As will be described, the device 40 is a fluid pressurizing device which can be used in connection with balloon catheters or the like. The fluid displacement device 40 is designed somewhat differently than the prior art device 10 shown in FIG. 1, and hence provides several advantages over that which is shown in FIG. 1. As discussed above, FIG. 1 corresponds to FIG. 2 of U.S. Pat. No. 5,713,242. U.S. Pat. No. 5,713,242 is hereby incorporated herein in its entirety by reference.

Figure 4:
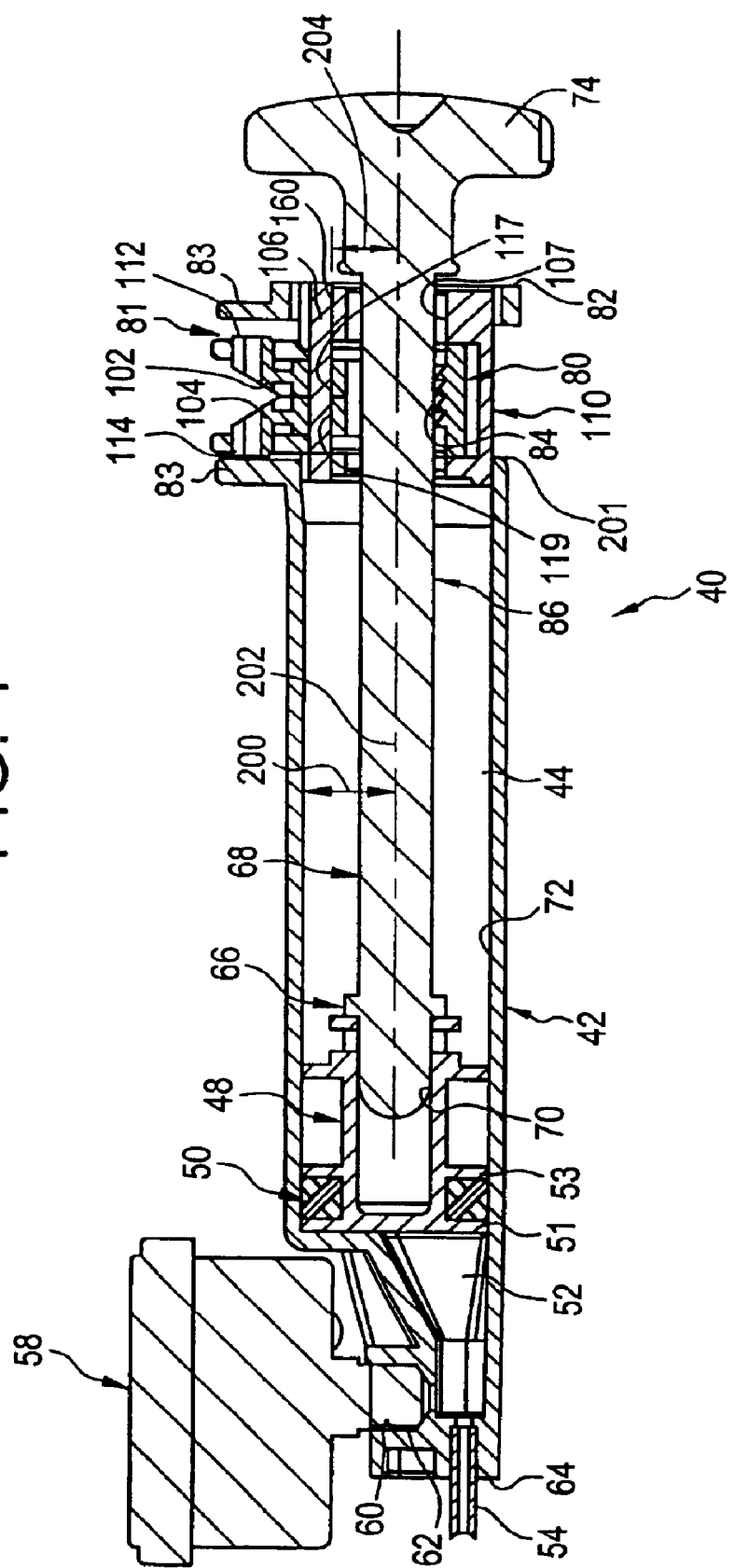
FIG. 4 is a cross-sectional view of the actuating mechanism illustrated in FIGS. 2 and 3, taken along line 4—4 of FIG. 3.

The device shown in FIGS. 2–5 has a generally cylindrical syringe body or housing 42 which provides a fluid displacement chamber 44 (see specifically FIG. 4). Preferably, the housing 42 is transparent thereby facilitating the viewing of fluid in the fluid displacement chamber 44 during fluid aspiration or dispensing. The housing 42 is formed of plastic, and may be molded from polycarbonate or another type of resin. The housing 42 has volumetric indicia thereon, such as at location 46 indicated in FIG. 2, so that a physician can readily determine the volume of fluid contained in the chamber 44. As shown, handles 39 are provided on the housing 42 to facilitate gripping of the device and operation thereof.

Figure 5:
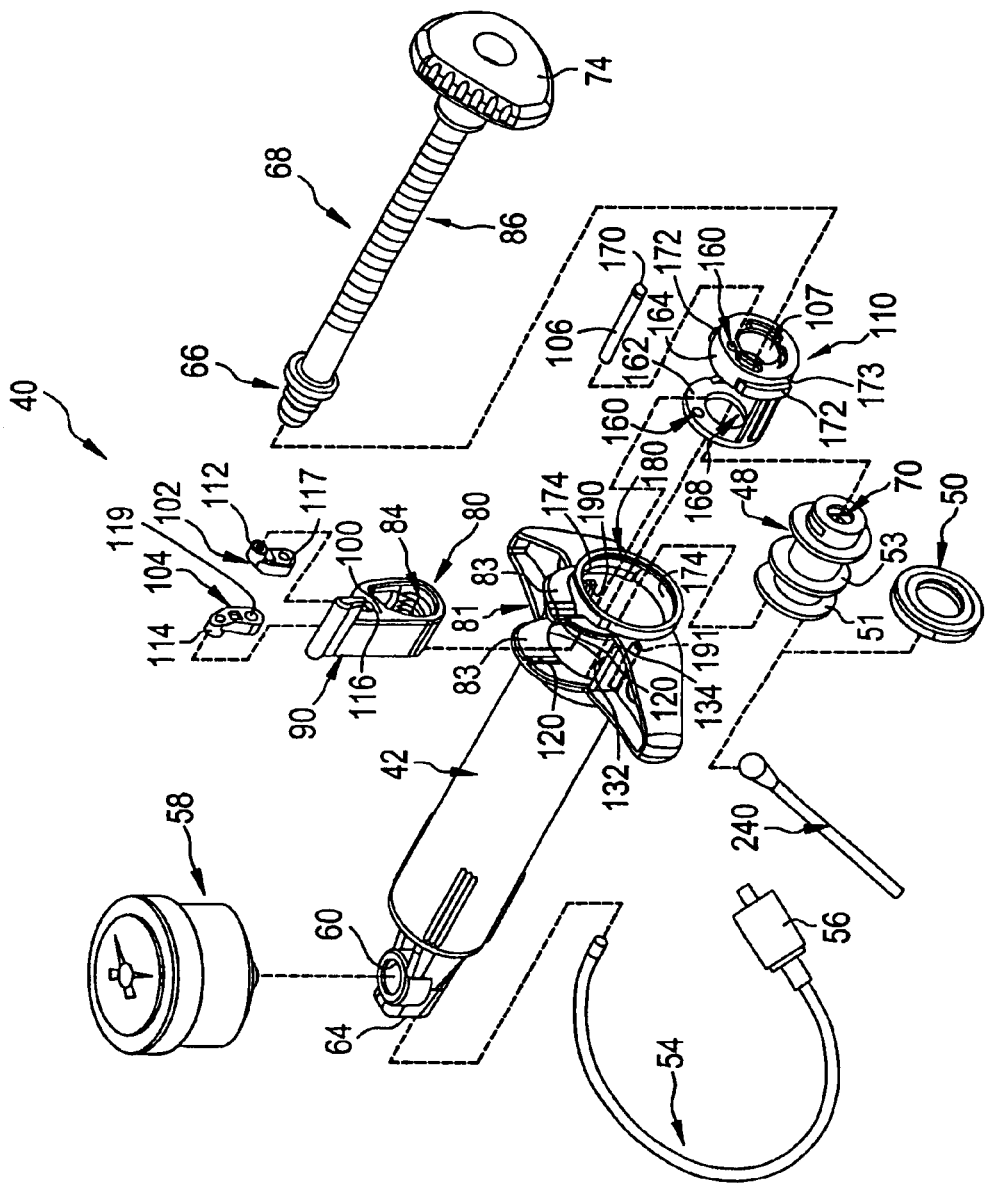
FIG. 5 is an exploded perspective view of the actuating mechanism illustrated in FIGS. 2–4.
Figure 8:
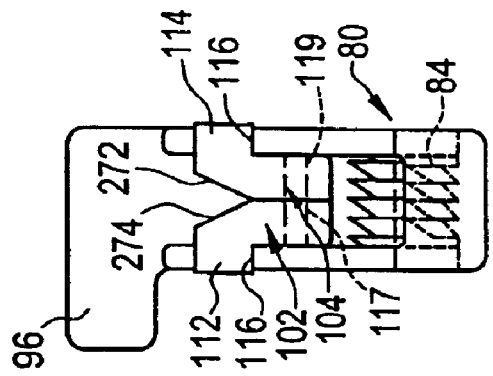
FIGS. 8–11 are sequential views showing progressive steps in assembly of coupling and nut structures of the actuating mechanism shown in FIGS. 2–5.
Figure 9:
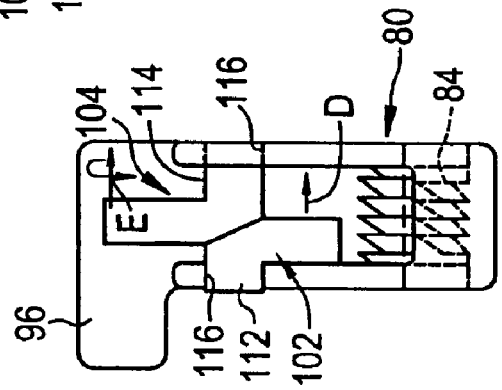

A piston 48 is slidably displaceable within the fluid displacement chamber 44 (i.e. in the housing 42). A sealing member 50, such as a quad ring, is disposed on the piston 48. As shown in FIG. 4, preferably the sealing member 50 is disposed between two walls 51 and 53 provided on the piston 48. As will be described more fully later hereinbelow, a lubricant may be used to place the sealing member 50 on the piston 48. The sealing member 50 is configured for pressure retention and the prevention of leakage of fluid past the piston 48 in the fluid displacement chamber 44. As shown in FIG. 4, the housing 42 includes a fluid conduit 52 which is in communication with the fluid displacement chamber 44. The fluid conduit 52 is also in communication with a hose 54 that is connected to balloon catheter structure (not shown), a fluid supply reservoir (not shown) or some other suitable structure depending on the application. As shown in FIG. 5, a connector 56 may be provided on the hose 54, between the fluid conduit 52 and the balloon catheter.

As shown in FIG. 4, the fluid conduit 52 also communicates with a pressure gauge assembly 58. Preferably, the pressure gauge assembly 58 is engaged directly with the housing 42, such as threadably engaged with a threaded bore 60 (see FIGS. 4 and 5) thereon. To this end, the pressure gauge assembly 58 is provided with a threaded portion 62 which threadably engages the threaded bore 60 on the housing 42. An adhesive may be provided between the threaded portion 62 and the threaded bore 60 to lockingly and sealingly engage the parts together. As shown in FIGS. 4 and 5, the threaded bore 60 is provided generally proximate an end 62 of the housing 42 such that, when installed, the pressure gauge assembly 58 is disposed generally proximate a distal end 64 of the device 40. The pressure gauge assembly 58 is configured to provide a physician with an indication of the pressure in the fluid conduit 52 and balloon catheter. The pressure gauge assembly 58 can be of any suitable type for either angioplasty or for other employment of the device 40. The fact that the device 40 is configured such that the pressure gauge assembly 58 engages directly with the housing 44 provides increased visibility proximate the distal end 64 of the device 40. Such visibility become important when a physician is to purge all the air bubbles from the fluid displacement chamber 44 before using the device 40 to dispense fluid.

As best shown in FIG. 4, the piston 48 is mounted on an unthreaded pilot nose end 66 of a threaded screw plunger 68. The pilot nose end 66 is configured to freely rotate in a central journal cavity 70 of the piston 48. The piston 48 is mounted on the pilot nose end 66 of the threaded screw plunger 68 in a snap-action, interference coupling which prevents the pilot nose end 66 from withdrawing or backing out of the central journal cavity 70 of the piston 48 when the threaded screw plunger 68 is retracted to aspirate fluid into the fluid displacement chamber 44. The pilot nose end 66 is freely rotatable relative to the coupled piston 48 so that the piston 48 is linearly advanced or retracted without rotation relative to rotation of the threaded screw plunger 68 in threaded advancement or retraction, in order to prevent any leakage of pressurized fluid from the fluid displacement chamber 44 between the sealing member 50 and an internal wall 72 (see FIG. 4) of the housing 42. As shown in FIGS. 2–5, the threaded screw plunger 68 preferably includes an integral palm knob 74 which facilitates movement of the threaded screw plunger 68 as will be described in more detail hereinbelow.

A nut member 80 is disposed in the housing 42, generally near a rearward end 82 of the housing 42. As shown in FIGS. 2–5, the nut member 80 is preferably mounted in an aperture 81 in the housing 42, where the aperture 81 is provided between a pair of spaced flanges 83. As shown in FIG. 5, the nut member 80 includes partially formed threads 84. The threads 84 are selectively engageable and disengageable from a threaded portion 86 of the threaded screw plunger 68 by displacement of the entire nut member 80 in a translating motion as shown in the progression from FIG. 6 to FIG. 7. The motion of the nut member 80 in moving between the positions of FIGS. 6 and 7 is in actuality that of a diminishing curved path and, as such, is not truly linear.

The nut member 80, and specifically the threads 84 thereof, is selectively disengageable from the threaded screw plunger 68 in order to permit manual rapid displacement of the threaded screw plunger 68 and piston 48, for example, for aspiration of saline solution into the fluid displacement chamber 44 from a fluid supply reservoir (not shown) which may be connected to the hose 54. The disengagement of the nut member 80 from the threaded screw plunger 68 also enables rapid advancement of the threaded screw plunger 68 and piston 48, for example, to discharge solution through the hose 54 to inflate an angiolplasty balloon (not shown) which has been previously positioned within a blood vessel or heart valve using a balloon catheter. Rapid retraction of the threaded screw plunger 68 and piston 48 may also enable swift aspiration of fluid into the fluid displacement chamber 44 for rapid deflation of an angiolplasty balloon. Also, prior to connection to the catheter, the threaded screw plunger 68 may be operated to insure that all air bubbles have been eliminated from the fluid which is contained in the fluid displacement chamber 44.

In order to facilitate the selective engagement (see FIG. 7) or disengagement (see FIG. 6) of the threads 84 of the nut member 80 with the threaded portion 86 of the threaded screw plunger 68, the nut member 80 is selectively displaceable by manually activating actuation structure 90 on the nut member 80. The actuation structure 90 preferably includes a grip portion 96 which is provided on the nut member 80, wherein displacement of the nut member 80 is achieved by grasping and displacing the grip portion 96. Displacement of the nut member 80 is preferably guided along a translating motion between the positions shown in FIGS. 6 and 7.

Figure 12:
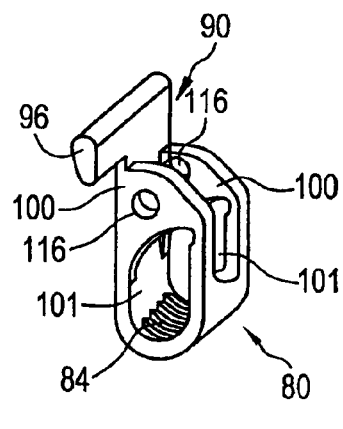
FIG. 12 is a perspective view of a nut member component of the actuating mechanism shown in FIGS. 2–5.
Figure 13:
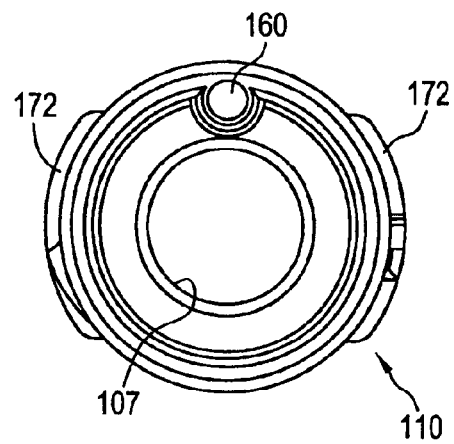
FIG. 13 is a front, elevational view of a carrier member component of the actuating mechanism shown in FIGS. 2–5.

As viewed in FIGS. 6, 7 and 12, the threads 84 of the nut structure 80 are formed in a lower base portion of the nut structure 80, and the nut structure 80 includes an upstanding, bifurcated portion which provides a pair of spaced, elongate arm or mounting portions 100 (see specifically FIG. 12). The mounting portions 100 in effect define carriage structure, and are generally integral with the threads 84. Each of the mounting portions 100 has an aperture 101 therein, through which the threaded screw plunger 68 extends (see specifically FIGS. 4, 6 and 7).

FIG. 6 illustrates the released position of the nut structure 80 in which the threads 84 of the nut member 80 are disengaged from the threaded portion 86 of the threaded screw plunger 68. In such position, the threaded screw plunger 68 may be axially translated in the fluid displacement chamber 44 by sliding the threaded screw plunger 68 forward or by pulling the fluid displacement chamber 44 back. No rotation of knob 74 is needed. In essence, macro-movement of the threaded screw plunger 68 is possible.

In contrast, FIG. 7 illustrates the engaged position of the nut structure 80 in which the threads 84 of the nut member 80 are engaged with the threaded portion 86 of the threaded screw plunger 68. In such position, the threaded screw plunger 68 may be axially translated in the fluid displacement chamber 44 only by rotating knob 74. In essence, only micro-movement of the threaded screw plunger 68 is possible. As described above, the pilot nose end 66 of the threaded screw plunger 68 is configured to freely rotate in the central journal cavity 70 of the piston 48. Hence, rotation of the threaded screw plunger 68 while the threads 84 of the nut member 80 are engaged with the threaded portion 86 of the threaded screw plunger 68 does not cause the piston 48 to rotate in the fluid displacement chamber 44 in the housing 42.

Figure 11:
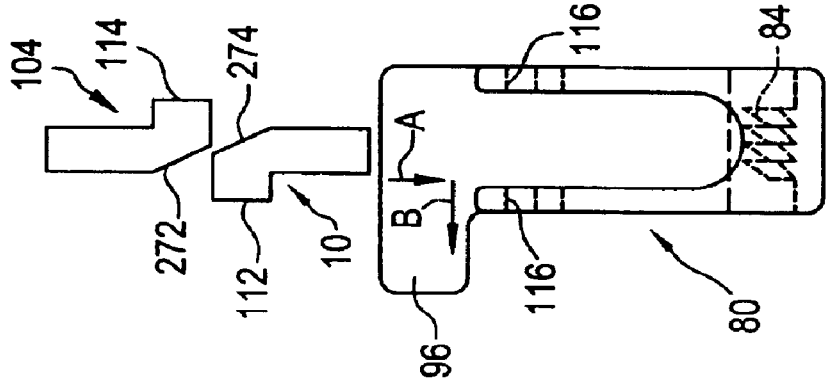

Movement of the nut structure 80 between the released (FIG. 6) and the engaged position (FIG. 7) is guided to the threaded screw plunger 68 under the guidance of a link structure. As shown in FIGS. 6 and 7 (see also FIGS. 3–5), the link structure may consist of two link members 102 and 104 which are positioned and configured to operate in tandem. As shown in FIGS. 4 and 11, the link members 102 and 104 are secured in adjacent, opposing alignment by a pivot pin 106 which is engaged with a carrier member 110 that is received in the housing 42, which will be described in more detail later hereinbelow. The pin 106 extends axially through apertures 117 and 119 (see FIGS. 4 and 5) provided in the link members 102 and 104. The link members 102 and 104 are journaled on the pin 106 at one end of the link member 102, 104. At an opposite end of each link member 102 and 104, an integral shaft portion 112 and 114, respectively, of each link member 102, 104 is journaled within apertures 116 provided in the respective mounting arms 100 of the nut member 80. The shaft portions 112 and 114 thus rotatably couple the link members 102 and 104 to the nut structure 80, as shown in FIGS. 6 and 7, so that motion of the nut member 80 is constrained by the link members 102 and 104, which must rotate on the pin 106.

When the nut member 80 is most tightly engaged with the threaded screw plunger 68 as shown in FIG. 7, the translating motion of the grip portion 96 of the nut member 80 preferably terminates in an "over-center" locking position which ensures that any slight motion of the nut member 80 which could be induced by fluid pressure in the fluid displacement chamber 44 imposed on piston 48 will result in tighter engagement of the threaded screw plunger 68 and nut member 80 rather than any tendency for loosening or disengagement thereof.

The engaged position of FIG. 7 is preferably releasably locked by a pair of detent structures in the form of raised ribs 120 projecting inwardly between each of the upstanding flanges 83 on the housing 42. Each of the shaft portions 112 and 114 of the link members 102 and 104, respectively, projects slightly through the aperture 116 in the mounting arms 100 of the nut member 80, so that ends of the shaft portions 112 and 114 must slide across the raised ribs 120 on the flanges 83 on the housing 42 in an interference engagement and resilient wedging motion which slightly spreads the flanges 83. Thereafter, deliberate forceful manual movement of the grip portion 96 of the nut member 80 is required to drive the vertical sliding movement of the nut member 80 between the engaged position shown in FIG. 7 and the released position shown in FIG. 6. Accordingly, the threaded engagement position of the nut member 80 shown in FIG. 7 in which the shaft portions 112 and 114 of the link members 102 and 104 have cleared the respective ribs 120 on the flanges 83 of the housing 42 will thereafter require manual force to be applied to the grip portion 96 for the link members 102 and 104 to again clear the ribs 120 (in the other direction) to cause the nut member 80 to translate into the released position shown in FIG. 6.

As shown in FIG. 6, when the nut member 80 is fully translated into the released position, preferably an exterior surface 130 of the nut member 80 becomes abutted against a protrusion 132 which is provided on a flange 134 provided on the housing 42. The protrusion 132 serves as a stop for the sliding motion of the nut structure 80 into the released position, wherein the threads 84 of the nut member 80 are generally disengaged from the threaded portion 86 of the threaded screw plunger 68.

As discussed above, the pin 106 which extends through the apertures 117 and 119 in the link members 102 and 104, respectively, is engaged with a carrier member 110 that is received in the housing 42. The carrier member 110 and its engagement with the housing 42 will now be described in more detail. As shown in FIGS. 5 and 13–20, the carrier member 110 may be provided in the form of a generally hollow, generally cylindrical part. The carrier member 110, like the housing 42, may be formed of plastic. In fact, the carrier member 110 and the housing 42 may be formed of the same resin.

As shown in FIGS. 4, 5, 13, 14, 18 and 20, the carrier member 110 is provided with an aperture 160 through which the pin 106 extends. The carrier member 110 also is provided with an aperture or bore 107 through which the threaded screw plunger 68 extends. Preferably, the radius of the bore 107 in the carrier member 110 is not more than the radius of the fluid displacement bore of the device. The carrier member 110 supports the pin 106, and the pin 106 engages the link members 102 and 104. Specifically, the carrier member 110, being generally hollow, has two spaced apart walls 162, 164 each having an aperture 160 therein for receiving the pin 106.

Figure 14:
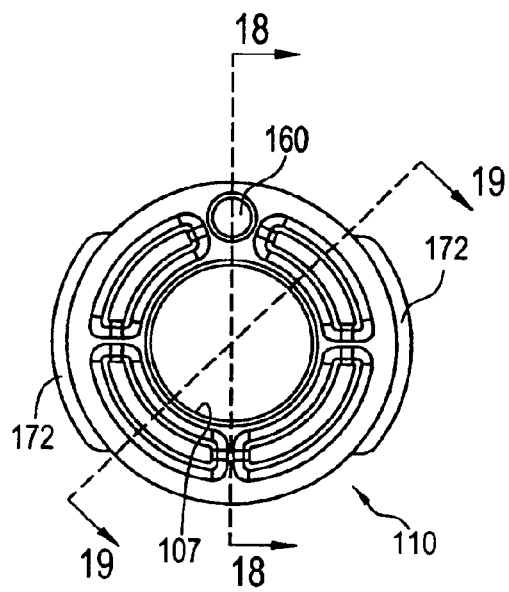
FIG. 14 is a rear, elevational view of the carrier member.
Figure 15:
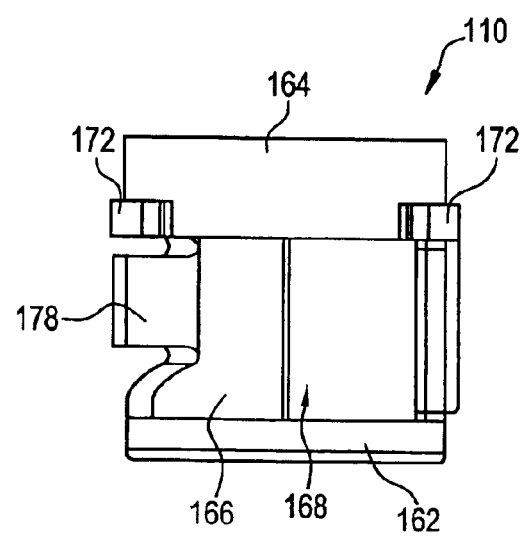
FIG. 15 is top, plan view of the carrier member.
Figure 16:
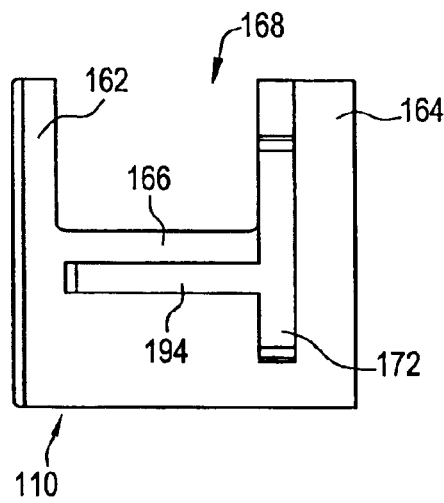
FIG. 16 is a side, elevational view of the right side of the carrier member.
Figure 17:
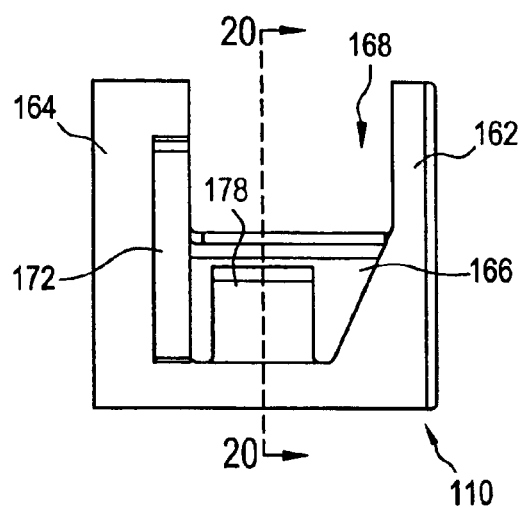
FIG. 17 is a side, elevational view of the left side of the carrier member.
Figure 18:
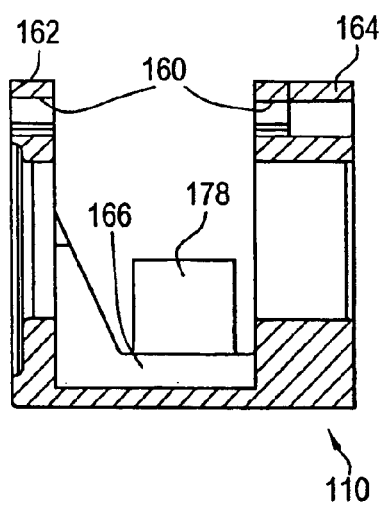
FIG. 18 is a cross-sectional view of the carrier member, taken along line 18—18 of FIG. 14.
Figure 19:
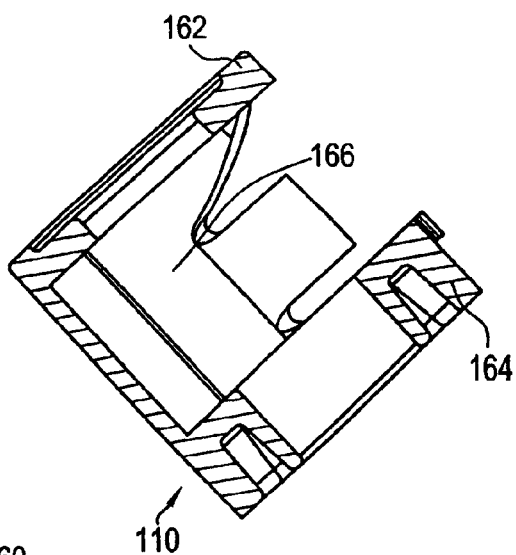
FIG. 19 is a cross-sectional view of the carrier member, taken along line 19—19 of FIG. 14.
Figure 20:
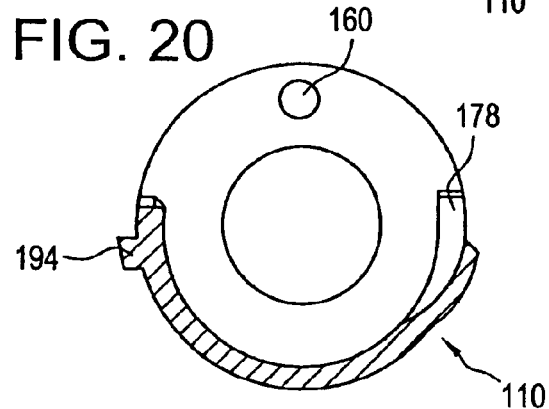
FIG. 20 is a cross-sectional view of the carrier member, taken along line 20—20 of FIG. 17.

As shown in FIG. 5, wall 162 defines the front surface of the carrier member 10 (see also FIG. 13, which provides a view of the front of the carrier member 110), and wall 164 defines the rear surface of the carrier member 110 (see also FIG. 14, which provides a view of the rear of the carrier member 110). A partial wall 166 extends between the front and rear walls 162 and 164 of the carrier member 110. A cut out 168 is defined between the walls 162 and 164, and the nut member 80 is disposed in the cut out 168. The pin 106 extends through the aperture 160 provided in the carrier member 110 and through the apertures 117 and 119 provided in the link members 102 and 104, and the carrier member 110 generally retains the pin 106 such that the pin 106 does not readily move axially. As shown in FIG. 5, the pin 106 may be provided with a knurled end portion 170 which assists in preventing the pin 106 from translating axially once it is installed in the carrier member 110.

As shown in FIGS. 5 and 13–18, protruding surfaces 172 are provided on an external surface 173 of the carrier member 110, generally proximate the rear end of the carrier member 110. Corresponding cut outs 174 are provided in the housing 42, at the rearward end 82 thereof, for receiving the protruding surfaces 172 provided on the carrier member 110. Preferably, the cut outs 174 in the housing 42 and the protruding surfaces 172 on the carrier member 110 provide that the carrier member 110 can be inserted in a bore 180 in the end 82 of the housing 42, and then rotated to secure the carrier member 110 in the housing 42. Specifically, the carrier member 110 and housing 42 are configured such that the carrier member 110 is installable through the rear portion of the housing 42 in the bore 180 in the housing 42 via a quarter-turn bayonet arrangement, wherein the carrier member 110 is axially inserted in the bore 180 and then given a one-quarter turn to lock the carrier member 110 in place.

The carrier member 110 includes a latching finger 178 which is formed as part of the partial wall 168 which extends between the front and rear walls 162, 164 of the carrier member 110. The latching finger 178 preferably engages an inwardly extending flange 190 provided on an internal wall of the housing 42 (see FIG. 5). Specifically, the latching finger 178 engages and clears the inwardly extending flange 190 on the housing 42 in a manner which generally locks the carrier member 110 in place in the bore 180 in the housing 42. Preferably, the latching finger 178 and inwardly extending flange 190 are configured such that an audible noise is produced as the latching finger 178 engages and clears the inwardly extending flange 190. The noise is loud enough to provide an audible indication to an assembler of the device that the carrier member 110 is fully installed in the bore 180.

Preferably, another inwardly extending flange 191 is provided on the internal wall of the housing 42 exactly opposite flange 190 (i.e. 180 degrees from flange 190, along the interior wall of the housing 42). A protruding surface 194 is provided on the external surface 173 of the carrier member 110, generally extending from protrusion 172 of the carrier member 110 toward the front end of the carrier member 110. When the carrier member 110 is inserted in the bore 180, the protruding surface 194 contacts edge 201 (see FIG. 4) of the housing 42 to prevent the carrier member 110 from installing too far axially into the bore 180. In other words, engagement of the protruding surface 194 with edge 201 limits axial travel of the carrier member 110 in the bore 180 during installation. Once the protruding surface 194 contacts edge 201, the carrier member 110 is rotated such that it becomes fully installed. Preferably, not only does the latching finger 178 of the carrier member 110 engage and clear the inwardly extending flange 190 on the housing, but the protruding surface 194 on the carrier member 110 engages the opposite inwardly extending flange 191 on the internal surface of the housing 42. When the carrier member 110 is fully installed in the bore 180, the carrier member cannot be readily axially withdrawn from the bore 180, nor can the carrier member 110 be readily rotated in either rotational direction relative to the housing 42. When the carrier member 110 is properly installed in the housing 42, the cut out 168 in the carrier member 110 is generally aligned with the aperture 81 in the housing 42.

The nut member 80 (and link members 102 and 104 engaged therewith) is received in the cut out 168 in the carrier member 110 and the aperture 81 in the housing 42 such that the grip structure 96 of the nut member 80 generally extends out the aperture 81 in the housing 42 for easy access. The carrier member 110 is securably engaged relative to the housing 42, and the pin 106 is retained by the carrier member 110. The pin 106 extends through the link members 102 and 104 which are retained on the nut member 80. Hence, the nut member 80 is pivotable between the positions shown in FIGS. 6 and 7 within the aperture 81 in the housing 42 and generally within the cut out 168 in the carrier member 110.

The carrier member 110 is configured to withstand in use forces as the threaded screw plunger 68 is translated forward in the fluid displacement chamber 44. The carrier member 110 permits the device 40 to be assembled from the rear of housing 42 (i.e. is rear loaded), as will be described more fully later hereinbelow in connection with describing assembly of the device 40. Additionally, as shown in FIG. 4, the carrier member 110 provides that a distance 200 from a center line 202 of the threaded screw plunger 68 can be greater than a distance 204 from the center line 202 of the threaded screw plunger 68 to pin 106.

Still further, the design of the device 40, by including the carrier member 110, provides that many of the parts are universal such that they are compatible with devices of different sizes. Specifically, the nut member 80, link members 102 and 104 and threaded screw plunger 68 may be used in association with different sized devices, specifically devices with different sized fluid displacement chambers 44. The carrier member 110 shown in the FIGURES is designed to be used with fluid displacement chambers which are as large as that shown in the FIGURES or which are smaller than that shown in the FIGURES. Of course, a larger sized device can be provided so long as a corresponding larger end bore 180 and carrier member are provided as well.

A method of assembling the device 40 will now be described. To assemble the device 40, hose 54 may be affixed to the housing 42. Then, the pressure gauge assembly 58 is engaged with the housing 42. Specifically, adhesive may be disposed on the threaded portion 62 of the pressure gauge assembly 58, and the threaded portion 62 threadably engaged with the threaded bore 60 in the housing 42. Subsequently, the sealing member 50 is fit onto the piston 48. To facilitate this, a lubricant can be used as illustrated by applicator 240 shown in FIG. 5. Then, the piston 48 is slipped into bore 180 in the housing 42 (i.e. from right-to-left in FIG. 4). In other words, the piston 48 is rear loaded into the device 40. Then, the carrier member 110 is installed on the housing 42, also from the rear portion of the housing 42. As described above, this installation may be via a quarter-turn bayonet style installation wherein the carrier member 110 is axially inserted into the bore 180 and then is rotated a quarter turn to lock the carrier member 110 in place relative to the housing 42. As described above, preferably the locking finger 178 on the carrier member 110 emits a snapping or clicking sound once the carrier member 110 is fully and properly installed. When the carrier member 110 is properly installed in the housing 42, the cut out 168 in the carrier member 110 is generally aligned with the aperture 81 in the housing 42. Subsequently, the nut member 80 can be installed in the carrier member 110. However, before the nut member 80 is installed in the carrier member 110, the link members 102 and 104 must be installed in the nut member 80.

Figure 10:
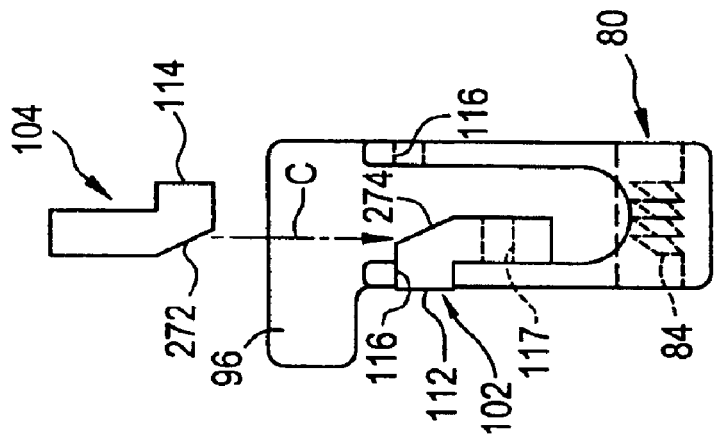

FIGS. 8–11 illustrate installation of the link members 102 and 104 in the nut member 80. While FIGS. 8–11 illustrate an example where link member 102 is first inserted in the nut member 80 followed by the insertion of link member 104, installation can begin with link member 104 followed by link member 102. With reference to FIGS. 8–11, installation of the link members 102 and 104 begins by inserting link member 102 between the mounting arms 100 of the nut member 80 (as represented by arrow A in FIG. 8), and then inserting the shaft portion 112 of the link member 102 into the aperture 116 in the nut member 80 (as represented by arrow B in FIG. 8) after which the aperture 117 is aligned with the aperture 106 provided in the carrier member 110 (see FIG. 9). Thereafter, the other link member 104 is inserted between the mounting arms 100 (as represented by arrow C in FIG. 9) in an orientation such that an inclined clearance surface 272 of link member 104 is engaged or is only slightly away from of a corresponding inclined clearance surface 274 on link member 102 into the position shown in FIG. 10. In the illustrated embodiment, the conforming engagement of the clearance surfaces 272 and 274 orientates link member 104 in inverted orientation relative to the link member 102 so that the shaft portion 114 can be inserted sufficiently between the mounting portions 100 for alignment with the aperture 116 provided in nut member 80, as shown in FIG. 10. Following passage of the shaft portion 114 of link member 104 into the aperture 116 (as represented by arrow D in FIG. 10), the link member 104 is rotated (as represented by arrow E in FIG. 10) under the guidance of aperture 116, until link member 104 becomes aligned in mirror image orientation with link member 102 including oppositely aligned inclined clearance surfaces 272 and 274. This position is shown in FIG. 11. Thereafter, the nut member 80, with the link members 102 and 104, can be inserted into the cut out 168 in the carrier member 110, and the pin 106 can be inserted into the aperture 106 in the carrier member and through the apertures 117 and 119 provided in the link members 102 and 104, thereby generally securing the link members 102 and 104 to the carrier member 110 in pivotable relationship.

After nut member 80 has been installed in the carrier member 110 and the pin 106 installed through the link members 102 and 104, the threaded screw plunger 68 is generally axially inserted into the rear end of the housing 42 into engagement with the piston 48. Specifically, the nose end 66 of the threaded screw plunger 68 is inserted through the bore 107 in the carrier member 110, through the bore 101 provided in the nut member 80, and into snap-fit engagement with the piston 48 within the fluid displacement chamber 44. Thereafter, the device 40 is operable.

As described hereinabove, the device 40 is configured to be assembled from the rear. Specifically, both the piston 48 and carrier member 110 are installed in the rear of the housing 42. By providing that the device 40 is assembled from the rear, the housing 42 can be provided as a single, integral piece. The front portion of the housing 42 can be molded as part of the housing 42, and no extra fittings or clamping covers need to be used to mount the gauge to the housing. The gauge can be engaged directly with the housing 42. Hence, the design of the present invention reduces the number of parts and reduces labor. Additionally, there is no issue with regard to sealing the front of the device 40 because the front portion of the device is integral with the remainder of the housing 42. Moreover, visibility at the front of the device 40 is improved, and this is advantageous to a user who is attempting to prime the device 40 before use by purging all the air bubbles from the chamber 44. By providing that the housing 42 is molded as a single piece, the housing can be manufactured in a single molding operation, thereby reducing the cost of the components and the molds, creating less waste and streamlining the production and assembly process.

Furthermore, the design of the device 40, by including the carrier member 110, provides that many of the parts are universal such that they are compatible with devices of different sizes. Specifically, the nut member 80, link members 102 and 104 and threaded screw plunger 68 may be used in association with different sized devices, specifically devices with different sized fluid displacement chambers 44. The carrier member 110 shown in the FIGURES is designed to be used with fluid displacement chambers which are as large as that shown in the FIGURES or which are smaller than that shown in the FIGURES. Of course, a larger sized device can be provided so long as a corresponding larger end bore 180 and carrier member are provided as well.

While an embodiment of the present invention is shown and described, it is envisioned that those skilled in the art may devise various modifications of the present invention without departing from the spirit and scope of the foregoing disclosure.

What is claimed is:

1. A method of assembling an actuating mechanism, said method comprising: sliding a piston into an end of a housing; sliding a carrier member into the housing through the end of the housing; rotating the carrier member thereby providing that the carrier member generally locks in place with respect to the housing; installing link members in a nut member; placing the nut member generally into the carrier member; engaging a pivot pin with the carrier member and the link members; sliding a plunger into the end of the housing through the nut member and carrier member; and engaging the plunger with the piston.

2. A method as recited in claim 1, further comprising engaging a hose with an opposite end of the housing.

3. A method as recited in claim 1, further comprising engaging a gauge with the housing.

4. A method as recited in claim 1, further comprising placing a sealing member on the piston.

* * * * *